United States Patent [19]

DiMarchi

[11] Patent Number: 4,616,078

[45] Date of Patent: Oct. 7, 1986

[54] PROCESS FOR PURIFYING PROINSULIN-LIKE MATERIALS

[75] Inventor: Richard D. DiMarchi, Carmel, Ind.

[73] Assignee: Eli Lilly and Company, Indianapolis, Ind.

[21] Appl. No.: 720,641

[22] Filed: Apr. 8, 1985

[51] Int. Cl.$^4$ .......................... C07K 3/12; C07K 3/18; C07K 3/20
[52] U.S. Cl. .................................... 530/305; 530/413; 530/415; 530/417; 530/808; 530/809; 530/825; 435/172.3; 435/240; 435/241
[58] Field of Search .......................... 260/112.7, 112 R

[56] References Cited

U.S. PATENT DOCUMENTS

| | | | |
|---|---|---|---|
| 3,649,456 | 3/1972 | de Bonneville et al. | 530/413 |
| 3,876,623 | 4/1975 | Jackson et al. | 260/112.7 |
| 3,907,676 | 9/1975 | Jorgensen | 260/112.7 |
| 4,430,266 | 2/1984 | Frank | 260/112.7 |

FOREIGN PATENT DOCUMENTS 2038340  7/1980  United Kingdom ............ 260/112.7

OTHER PUBLICATIONS

Rohm and Haas Bulletin—Amberlite Polymeric Adsorbents (Undated).
Pietrzyk et al., *Anal. Chem.*, 53, 1822–1828 (1981).
Pietrzyk et al., *J. Liq. Chromatog.*, 5, 443–461 (1982).

*Primary Examiner*—Howard E. Schain
*Attorney, Agent, or Firm*—William C. Martens, Jr.; Arthur R. Whale

[57] ABSTRACT

This specification describes a process for separating impurities from an impure mixture containing proinsulin-like material with substantially complete recovery of said proinsulin-like material, which comprises:

(1) applying said mixture to a reverse phase macroporous acrylate ester copolymer resin support at a pH of from about 7 to about 10; and
(2) eluting said proinsulin-like material from said support with an aqueous eluant having a pH of from about 8 to about 11 and containing from about 10% to about 30% by volume of an organic diluent selected from the group consisting of acetone, acetonitrile, and a combination of acetone and acetonitrile.

14 Claims, No Drawings

PROCESS FOR PURIFYING PROINSULIN-LIKE MATERIALS

BACKGROUND OF THE INVENTION

Proteins are biopolymers which are dependent upon structural stability to enact their specified function. Since a small change in solvent composition, pH, temperature, and salt concentration can often exert a significant and occasionally irreversible change in protein conformation, chromatographic protein purification has ideally been performed using resins exhibiting minimal non-specific, denaturing interactions. Classically, such resins have been extremely hydrophilic, having a water content often exceeding 80%. As a result of their hydrophilic nature, the resultant chromatographic resin particles are most susceptible to collapse, even under modest back-pressure. In addition, any non-specific adsorption can be difficult to displace due to an inability to effectively wash these hydrophilic resins with organic solvents. Consequently, one is confronted with a problem in the initial step of preparative purification of proteins from heterogeneous natural sources. The more desirable supports, due to their hydrophilic nature, are inappropriate for rapid throughput of viscous, sludge-laden, natural product mixtures. As a result, it has been necessary to use, at considerable additional expense, non-chromatographic methods for initial purification.

Amberlite ® XAD resins are polymeric macroreticular adsorbents, commercially produced by the Rohm and Haas Company. These resins have been designed for the separation of compounds based upon the varied affinity of the latter for a polymeric hydrophobic surface. Since XAD-type resins (1) have a large particle size (20–50 mesh) and (2) are extremely hydrophobic, any practical utilization of such resins in the chromatography of complex mixtures of structurally similar peptides and proteins would be surprising. Indeed, there is no report which details the operational parameters of these supports in protein purification. However, it is the foregoing two properties of the XAD-type resins which surprisingly make them exceptionally effective for the initial purification stages of highly impure sludge-laden mixtures containing both structurally diverse and structurally similar proteins. One would correctly expect that the large and heterogeneous particle sizes of XAD-type resins would substantially diminish their chromatographic performance due to the slow and unequal dynamics of interaction and, therefore, one would avoid the use of such resins in protein and polypeptide purification. It has been discovered, however, that this seeming deficiency in fact serves as an advantage when applied under precisely defined conditions to highly impure, sludge-laden materials containing proinsulin-like material.

Moreover, of added practical significance in the purification of such proinsulin-like material is the fact that XAD-type resins (1) are readily available at moderate cost, (2) are completely stable throughout the pH range of 1–13, and (3) are amenable to in-column regeneration with aqueous detergents and organic solvents.

The literature does not address, except in a most general manner, the use of XAD-type resins in the purification of proteins and polypeptides. Thus, for example, technical bulletins provided by the Rohm and Haas Company discuss adsorption of proteins on XAD-7 resin but fail to provide any enlightenment regarding the conditions of separation or efficiency of operation. Pietrzyk, D. J. and Stodola, J. D., *Anal. Chem.* 53, 1822–1828 (1981) were the first to analytically examine XAD-4, a co-polymer of polystyrene-divinylbenzene, for utilization with synthetic dipeptides. A further study [Pietrzyk, D. J., Cahill, W. J., and Stodola, J. D., *J. Liquid Chrom.* 5, 443–461 (1982)] with synthetic peptides as large as five residues revealed the possibility of achieving reasonably efficient preparative purification on XAD-4 resin which first had been crushed and sized to significantly smaller particles. Consequently, while these studies did indicate the ability to effectively chromatograph small peptides on macroporous hydrophobic resins, they did not address the question whether mixtures of substantially larger and vastly more complex proteins could be efficiently separated from highly impure mixtures using large particle size supports.

The difficulties of protein purification from highly impure sources have been especially evident with the advent of recombinant DNA technology and its particular suitability to the commercial production of peptides and proteins. Any commercially feasible expression of product by recombinant DNA methodology necessarily carries with it the requirement to isolate the recombinant DNA-sourced product from impurities contained in the originating fermentation broths as well as in the mixtures resulting from subsequent chemical and/or other treatments. The necessity for new commercial-scale protein purification methodology thus has become a high priority item.

An even more complicating factor in the purification of recombinant DNA-sourced proteins arises from the presence in many such proteins of cysteinyl residues. In most cases, following recombinant expression of cysteine-containing proteins, the cysteinyl sulfhydryls must be reversibly protected, generally by conversion to S-sulfonates, prior to commencing any protein purification. This essential conversion necessarily leads to the production of additional amounts of undesirable sludge-like impurities, in the presence of highly viscous denaturing agents, from which the desired protein must first be separated.

As a specific example, recombinant DNA-source insulin is available generally via either of two routes. By one route, the insulin A-chain and insulin B-chain are separately expressed and isolated, and the chains then are chemically combined to insulin. By the other route, a straight chain proinsulin precursor is expressed and isolated, and the product then is oxidatively renatured to proinsulin and the proinsulin enzymatically transformed to insulin.

Both of the above approaches to recombinant insulin production involve a similar sequence leading by chemical conversion and purification either to insulin A-chain S-sulfonate and insulin B-chain S-sulfonate ready for combination to insulin or to proinsulin S-sulfonate ready for disulfide interchange to proinsulin.

Any of the three S-sulfonates, insulin A-chain, insulin B-chain, or proinsulin, are in general obtained by the following sequence:

(1) Expression of product containing the desired peptide sequence joined at its amino terminal through a methionyl residue to an extraneous peptide sequence;

(2) Cleavage of the desired sequence from the extraneous portion using cyanogen bromide; and (3) Sulfitolysis of the peptide cysteinyl thiols to produce the corresponding S-sulfonates.

It is essential, in making processes of this nature commercially feasible, to discover methods that will permit removal of sludge, salt, organic solvents, and other contaminants from the desired product (whether such product is the final product or an intermediate along the way) with little or no loss of such product.

A highly advantageous process which forms the basis of this invention has been discovered for enhancing the purity of proinsulin-like material from highly impure stocks thereof obtained via recombinant DNA methods. The process involves subjecting the impure stock to reverse phase purification on a macroporous acrylate ester copolymer resin support.

SUMMARY OF THE INVENTION

Therefore, this invention is directed to a process for separating impurities from an impure mixture containing proinsulin-like material with substantially complete recovery of said proinsulin-like material, which comprises (1) applying said mixture to a reverse phase macroporous acrylate ester copolymer resin support at a pH of from about 7 to about 10; and (2) eluting said proinsulin-like material from said support with an aqueous eluant having a pH of from about 8 to about 11 and containing from about 10% to about 30% by volume of an organic diluent selected from the group consisting of acetone, acetonitrile, and a combination of acetone and acetonitrile.

DETAILED DESCRIPTION OF THE INVENTION

As noted hereinabove, the process of this invention is directed to the purification of highly impure mixtures containing proinsulin-like material. By the term "proinsulin-like material" as used herein is meant (1) proinsulin itself of whatever species, for example, human, bovine, or porcine; (2) precursors to proinsulin, such as reduced (—SH) proinsulin and S-protected proinsulin, for example, proinsulin S-sulfonate; (3) derivatives of proinsulin or its precursors, for example, structures which have been modified to lengthen and/or shorten the A-chain, the B-chain, the C-peptide, or a combination of any of the three; and (4) analogs of proinsulin or its precursors, for example, structures in which the proinsulin amino acid sequence has been modified by replacement of one or more amino acid residues.

The process of this invention involves the use of a macroporous acrylate ester copolymer resin as chromatographic support. Two such supports, highly suited for the purposes of this invention, are available from the Rohm and Haas Company and carry the designation XAD-7 and XAD-8. Of the two, XAD-7 is particularly preferred for the purposes of this invention.

The process of this invention can be divided into three customary chromatographic steps or stages. Only two of these, however, are required. Thus, the process must include a loading and a desorption step, and it may, and preferably does, include an intermediate washing step. Moreover, the process may be carried out in either batch or column mode, although, for the sake of efficiency of purification, it, of course, is much preferred to conduct the process under column conditions. Whether the process of this invention is carried out using the batch or column mode, the particular conditions which are key to its success and which form the basis of the discovery described herein remain constant.

The complex mixture containing proinsulin-like material used in the loading step of this invention generally is obtained as a result of a sequence of preceding treatment steps and ultimately as the result of expression by recombinant DNA methodology. Customarily, a product is expressed containing an amino acid sequence, at least part of which corresponds to that of proinsulin or a derivative or analog thereof. The expression product will be designed to contain a selective cleavage site to permit proinsulin-like material to be generated chemically or enzymatically from the longer chain expression product. Generally, the selective cleavage site will be represented by a methionine residue, and cleavage at the carboxyl terminal of such residue will be efficiently carried out in accordance with well recognized conditions using cyanogen bromide. The resulting mixture, as a result of fermentation followed by CNBr-cleavage, will contain a wide range of peptides along with an accompanying complex mixture of sludge and other materials and, relatively speaking, minor amounts of reduced proinsulin-like material.

The mixture then customarily is treated under recognized conditions in the presence of large amounts of urea (generally about 7M) to effect protective sulfitolysis of the free sulfhydryls of the reduced proinsulin-like materials. The resulting sludge-laden, urea-containing mixture, containing appreciable levels of organic solvents and exhibiting high conductivity, represents the typical material loaded onto the macroporous acrylate ester copolymer in batch or column mode in accordance with the process of this invention.

In carrying out loading of material of the kind described hereinabove, the pH of the sludge-laden, urea-containing mixture is adjusted to a range of from about 7 to about 10, and, preferably, from about 8 to about 9, and the resulting solution is brought into contact with the macroporous acrylate ester copolymer resin.

Upon completion of the loading stage, the resin preferably is washed with an aqueous buffer having a pH of from about 7 to about 8.5, and, preferably, about 8. Any of a wide range of buffering agents can be used, including, for example, Tris, ethylenediamine, and the like. A buffering agent of choice is ethylenediamine.

Upon completion of loading of the resin, or washing, if such step is included, the proinsulin-like material is eluted from the column free of sludge and of substantially increased purity and concentration. The mandatory conditions for practical elution of the adsorbed proinsulin-like material are the prescribed pH range and eluant composition. The pH must be in the range of from about 8 to about 11, and, preferably, from about 9.5 to about 10.5. The aqueous eluant must contain, on a volume basis, from about 10% to about 30% of acetone, acetonitrile, or a combination of the two. Preferably, the range of acetone or acetonitrile present in the eluant will be from about 15% to about 25%.

The entire process of this invention can be carried out over a wide range of temperatures, for example, anywhere from about 4° C. to about 45° C. Preferably, however, and for the sake of convenience, the process is conducted at ambient temperature.

The aqueous-organic solution obtained as eluate from the process of this invention contains proinsulin-like material free of contaminating sludge, urea, and salt, and of substantially greater purity when compared with the original mixture as applied to the macroporous acrylate ester copolymer resin. The resulting proinsulin-like material can be recovered from the eluate by routine techniques, or the solution itself can be used in further processing of the material.

The following examples are provided to illustrate the process of this invention. They are not intended to be limiting on the broad scope thereof.

EXAMPLE 1

PURIFICATION OF HUMAN PROINSULIN S-SULFONATE

The XAD-7 resin having 20–50 mesh peptide size (available from the Rohm and Haas Company) was wetted with acetone at 10 ml/gm for 6 hours at room temperature. The resin then was washed extensively and sequentially with acetone, 0.1N NaOH, water, 0.1N HCl, water, and 100mM ethylenediamine/7M urea, pH 8.0. The resin, while in the final urea wash, was packed into a 2.2×100 cm chromatographic column at a constant pressure of 15 psi. When properly packed, the column exhibited a homogenous mixture of the various sized resin particles.

A cell lysate containing a recombinant DNA-expressed chimeric protein was produced. The chimeric protein contained a leader sequence of amino acids joined via a methionine residue to an amino acid sequence corresponding to that of human proinsulin. The lysate first was treated with cyanogen bromide to effect cleavage of the chimeric protein at each methionine residue and thereby to liberate a molecule carrying the human proinsulin sequence, and then was treated under sulfitolysis conditions to sulfitolyze each cysteinyl residue present in the lysate reaction mixture.

A solution of 75 mg of the complex mixture of solids resulting from the foregoing was dissolved in 7M urea at pH 8.5. The solution was applied to the aforedescribed chromatographic column at room temperature with a flow rate of about 30 cm/hour. The column was loaded with an amount of material representing 1–2 gm of proinsulin S-sulfonate per liter of column volume.

The column then was washed with one column volume of 10 mM ethylenediamine, pH 8.5, after which the proinsulin S-sulfonate was eluted with 20 mM ethylenediamine, pH 9.5, containing 20% acetone. The proinsulin S-sulfonate was recovered in greater than 90% yield, was completely desludged, was free of organic contaminants from the CNBr cleavage, was free of sulfitolysis reagents, including urea, and was of approximately ten-fold greater purity.

EXAMPLE 2

IMPORTANT PARAMETERS IN THE PURIFICATION OF HUMAN PROINSULIN S-SULFONATE FROM FERMENTATION SOLIDS

Using fermentation solids produced as described in Example 1, a series of batch purifications was carried out. The procedure for batch purification involves washing the XAD-7 resin with organic solvents, aqueous acid, and aqueous base, and storing it as a wetted slurry in 10 mM ethylenediamine, pH 8.5, in a manner as described in Example 1. Prior to loading, the resin is poured free of extraneous solvent and weighed as wet particle. To a predetermined amount of resin was added with gentle shaking a loading solution consisting of fermentation solids containing proinsulin S-sulfonate at a known concentration and purity. The pH, temperature, conductivity and solvent composition of the loading solution were systematically varied. The kinetics of protein adsorption were monitored by analytical reverse phase chromatography of an aliquot of loading solution following its centrifugation. Once the desired loading had been achieved, the resin was poured free of extraneous loading solvent. Unloading of the adsorbed protein was initiated by washing each gram of loaded resin with 10 ml of 10 mM aqueous ethylenediamine at pH 8.5. The resin, once poured free of extraneous wash solvent, was suspended and shaken with the unloading solution. The solvent composition of the unloading solution and its ratio to the resin weight was varied systematically to maximize unloading yield and purity of the desired product. Unloading kinetics of the protein were determined, as in loading, by analytical reverse phase chromatography.

Using the batch methodology, the following Tables 1 to 5 demonstrate the importance of a variety of parameters of the process of this invention, including the characteristics of the particular resin, the loading conditions, and the elution conditions.

Table 1 following illustrates that XAD-7, an acrylate copolymer, is substantially superior in loading rate and efficiency to related polystyrene resins.

TABLE 1

| | Resin Selection | | | |
|---|---|---|---|---|
| Time, hours | Proinsulin S-sulfonate, Percent Adsorbed[a] | | | |
| | XAD-2[b] | XAD-4[b] | XAD-7[c] | HP-20[b] |
| 0 | 0 | 0 | 0 | 0 |
| 1.5 | 45 | 37 | 96 | 77 |
| 6 | 59 | 57 | 97 | 94 |
| 24 | — | — | 98 | 98 |

[a]Proinsulin S-sulfonate adsorption determined by reverse phase chromatographic analysis of the supernatant.
[b]Divinylbenzene-polystyrene copolymer.
[c]Divinylbenzene-acrylate ester copolymer.

As is noted from the above, on XAD-7 virtually all of the proinsulin S-sulfonate has been adsorbed after 1.5 hours or less, whereas the best of the polystyrene resins took three times as long to reach a comparable level.

Table 2 following illustrates certain of the pH and temperature conditions useful for column loading in accordance with the present invention.

TABLE 2

| | Rate of Proinsulin S-sulfonate Loading on XAD-7: Temperature and pH Effect | | | | | |
|---|---|---|---|---|---|---|
| | Proinsulin S-sulfonate, Percent Adsorbed | | | | | |
| Time, | pH (at 25° C.) | | | Temp, °C. (at pH 8) | | |
| hours | 7 | 8 | 9 | 4 | 25 | 45 |
| 0 | 0 | 0 | 0 | 0 | 0 | 0 |
| 1 | 71 | 66 | 73 | 60 | 66 | 73 |
| 3.5 | 91 | 88 | 90 | 78 | 88 | 93 |
| 5 | 97 | 94 | 96 | 86 | 94 | 97 |
| 24 | >99 | >99 | >99 | >99 | >99 | >99 |

Although an apparent loading occurs at a pH less than about 7, the phenomenon unexpectedly results in a condition which makes it extremely difficult if not impossible to elute the product from the column.

Table 3 following illustrates the criticality of pH selection and control for elution of product from the properly loaded column.

TABLE 3

| | Rate of Proinsulin S-sulfonate Unloading: pH Effect | | | | | |
|---|---|---|---|---|---|---|
| Time, hours | 2.5[b] | 4.5[b] | 6.5[b] | 8.5[c] | 9.5[c] | 10.5[c] |
| 0 | 0 | 0 | 0 | 0 | 0 | 0 |
| 2 | 0 | 0 | 0 | 35 | 46 | 61 |

TABLE 3-continued

| Rate of Proinsulin S-sulfonate Unloading: pH Effect | | | | | | |
|---|---|---|---|---|---|---|
| Time, hours | 2.5[b] | 4.5[b] | 6.5[b] | 8.5[c] | 9.5[c] | 10.5[c] |
| 6 | 0 | 0 | 0 | 30 | 47 | 60 |
| 24 | 0 | 0 | 0 | 24 | 49 | 59 |

[a] Conditions for desorption: To one gram of resin which had been loaded with a maximum amount of proinsulin S-sulfonate using the sulfitolysis reaction solution obtained from sulfitolysis of a CNBr-treated, recombinant DNA fermentation lysate were added, at 4° C., 5 ml of varying pH aqueous buffer containing 30% acetone.
[b] 10 mM ammonium phosphate aqueous-acetone buffer
[c] 10 mM ethylenediamine aqueous-acetone buffer Table 4 following illustrates the importance of the proper selections of organic solvent employed in product unloading.

TABLE 4

| | Rate of Proinsulin S-sulfonate Unloading: Organic Solvent Effect | | | |
|---|---|---|---|---|
| Time, hours | Proinsulin S-sulfonate, Percent Desorbed[a] Organic Solvent in Elution Buffer | | | |
| | Acetonitrile | Acetone | 1-Propanol | Ethanol |
| 0 | 0 | 0 | 0 | 0 |
| 1.5 | 37 | 50 | 7 | 10 |
| 3 | 38 | 55 | 8 | 12 |
| 5 | 39 | 55 | 8 | 13 |
| 24 | 36 | 52 | 12 | 9 |

[a] Conditions for desorption: To one gram of resin which had been loaded with a maximum amount of proinsulin S-sulfonate using the sulfitolysis reaction solution obtained from sulfitolysis of a CNBr-treated, recombinant DNA fermentation lysate were added, at 4° C., 6 ml of 10 mM ethylenediamine, pH 9.0, containing 30% organic in an aqueous solvent.

Table 5 following illustrates the critical importance of the range of organic solvent concentration.

TABLE 5

| | Rate of Proinsulin S-sulfonate Unloading: Organic Solvent Concentration Effect | | | | | |
|---|---|---|---|---|---|---|
| Time, hours | Proinsulin S-sulfonate, Percent Desorbed[a] Acetone, % of Elution Buffer | | | | | |
| | 0 | 5 | 10 | 15 | 20 | 30 |
| 0 | 0 | 0 | 0 | 0 | 0 | 0 |
| 1.5 | 25 | 52 | 65 | 70 | 81 | 60 |
| 6 | 31 | 55 | 70 | 68 | 79 | 60 |

[a] Conditions for desorption: same as indicated for Table 4, except that the buffer pH was increased to 10.5. The figures for percent desorbed noted above represent approximately the maximum available from non-column (batch) methodology.

I claim:

1. A process for separating impurities from an impure mixture containing proinsulin-like material with substantially complete recovery of said proinsulin-like material, which comprises:

(1) applying a complex, impure mixture obtained, without purification, as a result of recombinant DNA expression of a proinsulin-like material to a reverse phase macroporous acrylate ester copolymer resin support at a pH of from about 7 to about 10; and (2) eluting said proinsulin-like material from said support with an aqueous eluant having a pH of from about 8 to about 11 and containing from about 10% to about 30% by volume of an organic diluent selected from the group consisting of acetone, acetonitrile, and a combination of acetone and acetonitrile.

2. Process of claim 1, in which the proinsulin-like material has an amino acid sequence which corresponds to that of human proinsulin.

3. Process of claim 2, in which the proinsulin-like material is a precursor to proinsulin.

4. Process of claim 3, in which the proinsulin-like material is proinsulin S-sulfonate.

5. Process of claim 4, in which the macroporous acrylate ester copolymer support is XAD-7 or XAD-8.

6. Process of claim 5, in which the macroporous acrylate ester copolymer support is XAD-7.

7. Process of claim 6, in which the impure mixture containing proinsulin-like material is treated under batch conditions.

8. Process of claim 6, in which the impure mixture containing proinsulin-like material is treated under chromatographic column conditions.

9. Process of claim 8, in which the impure mixture containing proinsulin-like material is applied to the macroporous acrylate ester copolymer support at a pH of from about 8 to about 9.

10. Process of claim 8, in which, following application of the impure mixture to the column support and prior to elution, the support is washed with an aqueous buffer having a pH of from about 7 to about 8.5.

11. Process of claim 10, in which the proinsulin-like material is eluted from the support with an aqueous eluant having a pH of from about 9.5 to about 10.5.

12. Process of claim 11, in which the eluant contains from about 15% to about 25% by volume of an organic diluent selected from the group consisting of acetone, acetonitrile, and a combination of acetone and acetonitrile.

13. Process of claim 12, in which the organic diluent is acetone.

14. Process of claim 12, in which the organic diluent is acetonitrile.

* * * * *